United States Patent
Zhang

(10) Patent No.: US 7,496,402 B2
(45) Date of Patent: Feb. 24, 2009

(54) ATP PACING WITH ENTRAINMENT MONITORING

(75) Inventor: Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 503 days.

(21) Appl. No.: 10/835,078

(22) Filed: Apr. 29, 2004

(65) Prior Publication Data

US 2006/0149325 A1 Jul. 6, 2006

(51) Int. Cl.
*A61N 1/00* (2006.01)

(52) U.S. Cl. ...................................... 607/14

(58) Field of Classification Search ............. 607/4, 607/5, 9, 14, 32, 58, 59, 60; 600/510
See application file for complete search history.

(56) References Cited

U.S. PATENT DOCUMENTS

| | | | |
|---|---|---|---|
| 3,920,005 A * | 11/1975 | Gombrich et al. | 600/510 |
| 4,830,006 A | 5/1989 | Haluska et al. | |
| 5,161,529 A | 11/1992 | Stotts et al. | |
| 5,209,229 A | 5/1993 | Gilli | |
| 5,222,493 A | 6/1993 | Sholder | |
| 5,224,475 A | 7/1993 | Berg et al. | |
| 5,251,624 A | 10/1993 | Bocek et al. | |
| 5,324,310 A | 6/1994 | Greeninger et al. | |
| 5,330,505 A | 7/1994 | Cohen | |
| 5,342,402 A | 8/1994 | Olson et al. | |
| 5,350,410 A | 9/1994 | Kleks et al. | |
| 5,472,453 A | 12/1995 | Alt | |
| 5,548,619 A | 8/1996 | Horiike et al. | |
| 5,587,970 A | 12/1996 | Greenwood | |
| 5,662,688 A | 9/1997 | Haefner et al. | |
| 5,683,424 A | 11/1997 | Brown et al. | |
| 5,683,431 A | 11/1997 | Wang | |
| 5,836,971 A | 11/1998 | Starkweather | |
| 5,846,263 A | 12/1998 | Peterson et al. | |
| 5,855,593 A | 1/1999 | Olson et al. | |
| 5,871,512 A | 2/1999 | Hemming et al. | |
| 5,999,854 A | 12/1999 | Deno et al. | |
| 6,101,414 A | 8/2000 | Kroll | |
| 6,128,529 A | 10/2000 | Esler | |

(Continued)

FOREIGN PATENT DOCUMENTS

| EP | 1240918 A2 | 9/2002 |
|---|---|---|
| WO | WO-98/40122 A1 | 9/1998 |

OTHER PUBLICATIONS

"International Search Report and Written Opinion for Application No. PCT/US2005/014791, date mailed Aug. 9, 2005", 15 Pages.

*Primary Examiner*—George Manuel
(74) *Attorney, Agent, or Firm*—Schwegman, Lundberg & Woessner, P.A.

(57) ABSTRACT

A method and system for delivering anti-tachycardia pacing (ATP) is disclosed. During delivery of an ATP burst, an implantable cardiac rhythm management device is programmed to sense evoked responses and determine whether or not the ATP burst has entrained the heart by counting the number of successive pacing pulses achieving capture. This information may then be used by the device to adjust the manner in which the ATP therapy is delivered.

20 Claims, 2 Drawing Sheets

U.S. PATENT DOCUMENTS

| | | |
|---|---|---|
| 6,137,308 A | 10/2000 | Nayak |
| 6,167,308 A | 12/2000 | DeGroot |
| 6,192,275 B1 | 2/2001 | Zhu et al. |
| 6,330,477 B1 * | 12/2001 | Casavant ............ 607/14 |
| 6,400,986 B1 | 6/2002 | Sun et al. |
| 6,430,441 B1 | 8/2002 | Levine |
| 6,477,422 B1 | 11/2002 | Splett |
| 6,584,352 B2 * | 6/2003 | Combs et al. ............ 607/9 |
| 6,775,572 B2 | 8/2004 | Zhu et al. |
| 6,885,890 B2 | 4/2005 | Spinelli et al. |
| 2002/0058968 A1 | 5/2002 | Sun et al. |
| 2003/0083703 A1 | 5/2003 | Zhu et al. |
| 2003/0120315 A1 | 6/2003 | Spinelli et al. |
| 2003/0204210 A1 | 10/2003 | Ousdigian et al. |
| 2003/0208241 A1 | 11/2003 | Bradley et al. |
| 2005/0070967 A1 | 3/2005 | Zhu et al. |
| 2005/0090869 A1 | 4/2005 | Sun et al. |

* cited by examiner

ATP PACING WITH ENTRAINMENT MONITORING

FIELD OF THE INVENTION

This invention pertains to methods and system for treating cardiac arrhythmias with anti-tachycardia pacing.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia (AT), and atrial fibrillation (AF). The most dangerous tachyarrythmias, however, are ventricular tachycardia (VT) and ventricular fibrillation (VF). Ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus or point of re-entry directly into the myocardium. Ventricular tachycardia is typically characterized by distorted QRS complexes that occur at a rapid rate, while ventricular fibrillation is diagnosed when the ventricle depolarizes in a chaotic fashion with QRS complexes of constantly changing shape. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachyarrhythmias, including SVT's, VT, and VF. The electric shock terminates the tachyarrhythmia by depolarizing all of the myocardium simultaneously and rendering it refractory. A class of cardiac rhythm management devices known as an implantable cardioverter/defibrillator (ICD) provides this kind of therapy by delivering a shock pulse to the heart when the device detects fibrillation.

Another type of electrical therapy for tachycardia is anti-tachycardia pacing (ATP). In ATP, the heart is competitively paced with one or more pacing pulses in an effort to interrupt the reentrant circuit causing the tachycardia. ATP can be applied to either the ventricles or the atria. Modern ICD's typically have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible. It is commonly believed that only cardioversion/defibrillation will terminate fibrillation and certain high rate tachycardias, while ATP can be used to treat lower rate tachycardias. A tachyarrhythmia that is regarded as terminable by ATP therapy, based upon rate or other factors, will be referred to herein as either a terminable tachyarrhythmia or a tachycardia.

In most ICD's with ATP capability, fibrillation (VF or AF) is distinguished from tachycardia (VT or AT) using rate-based criteria so that ATP or shock therapy can be delivered as appropriate. The ventricular heart rate is usually measured by detection of the time between successive R waves (i.e., ventricular depolarizations), and the atrial rate is measured by detection of the time between successive P waves (atrial depolarizations). A measured heart rate is classified as a tachycardia when the rate is in a tachycardia zone, defined as a range of rates above a tachycardia detection rate (TDR) but below a fibrillation detection rate (FDR). A measured heart rate above the FDR, on the other hand, is in the fibrillation zone and is classified as either atrial or ventricular fibrillation. In a typical device, a tachyarrhythmia with a heart rate in the tachycardia zone is treated with ATP therapy in order to avoid an unnecessary painful shock to the patient, and a defibrillation shock is delivered if the pacing fails to terminate the tachyarrhythmia. The present disclosure relates to a method and apparatus for delivering ATP therapy in a manner that increases the likelihood that ATP therapy will terminate a tachyarrhythmia without resorting to a defibrillation shock.

DETAILED DESCRIPTION

The mechanism by which ATP therapy converts a tachyarrhythmia is through the entrainment of the heart by a burst of pacing pulses which results in the termination of the tachyarrhythmia. Entrainment of the heart means that a plurality of consecutive ATP pulses have succeeded in capturing the heart. When this occurs, the ATP burst has penetrated into the abnormal re-entrant cycles and is thus able to restore a normal pattern of excitation. The present disclosure deals with methods and apparatus for delivering ATP therapy in which the extent of entrainment is monitored and used to adjust the manner in which the ATP therapy is delivered.

1. Hardware Platform

Figure 1:
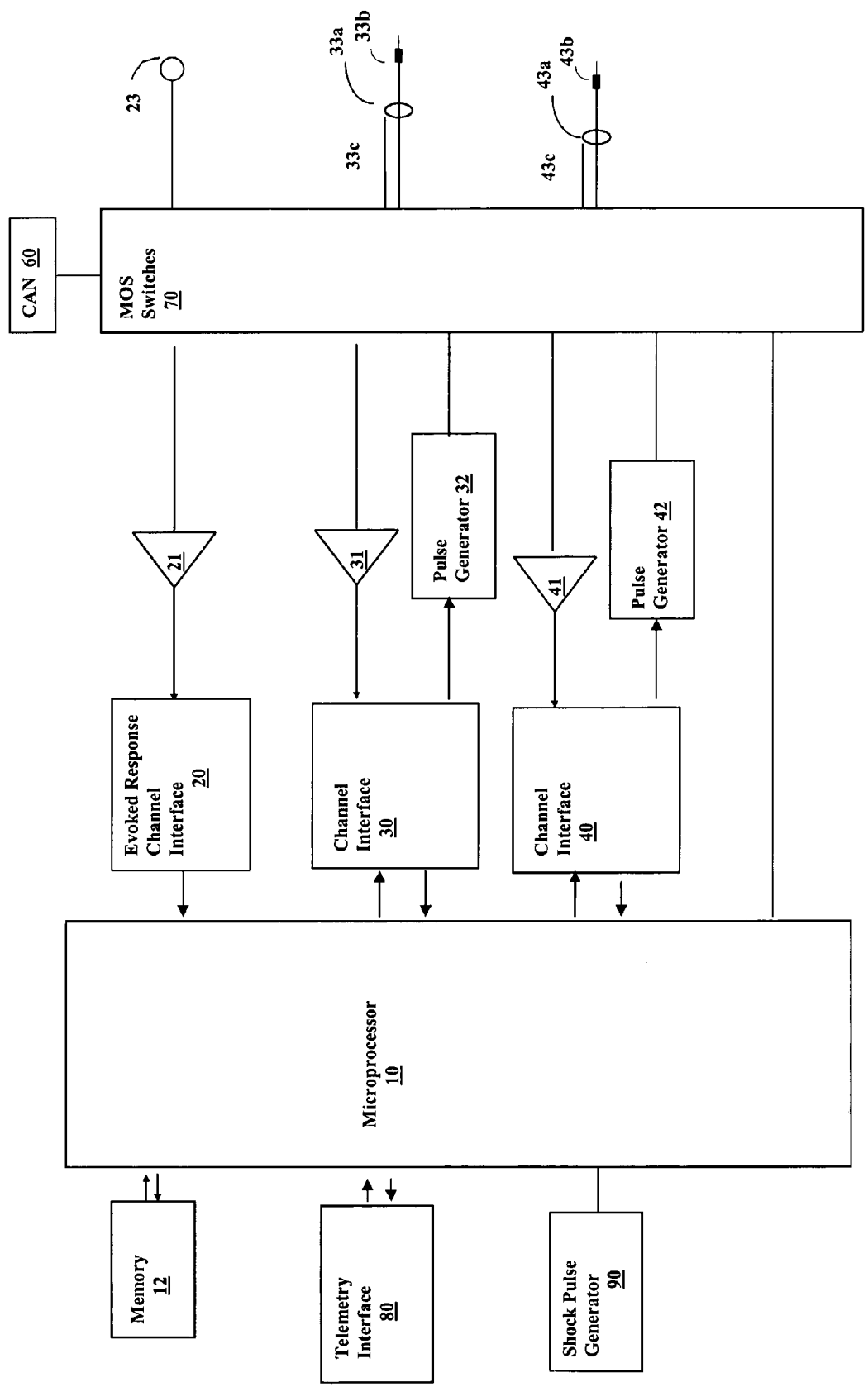
FIG. 1 is a block diagram of a cardiac rhythm management device with ATP and cardioversion/defibrillation capability.

FIG. 1 is a system diagram of a microprocessor-based cardiac rhythm management device with the capability of delivering cardioversion/defibrillation shocks as well as delivering anti-tachycardia pacing therapy to either the ventricles or the atria. The device may also be configured to deliver conventional (e.g., bradycardia) pacing as well. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer or other device via a wireless telemetry link.

The device shown in FIG. 1 has two sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. In an example configuration, one sensing/pacing channel includes ring electrode 43*a* and tip electrode 43*b* of bipolar lead 43*c*, sense amplifier 41, pulse generator 42, and a channel interface 40 while another sensing/pacing channel includes ring electrode 33*a* and tip electrode 33*b* of bipolar lead 33*c*, sense amplifier 31, pulse generator 32, and a channel interface 30. The channels may be configured as either atrial or ventricular channels. A dedicated evoked response sensing channel is also shown made up of a channel interface 20, sense amplifier 21, and electrode 23. The switch matrix may switch the input of the evoked response channel to the electrode 23 referenced to the device housing 60 or to any of the available electrodes so that an evoked response may be detected in either the atria or the ventricles.

The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator 90 is interfaced to the controller for delivering defibrillation shocks between an electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when a sense signal (i.e., a voltage sensed by an electrode representing cardiac electrical activity, sometimes called an electrogram signal) generated by a particular channel exceeds a specified intrinsic detection threshold. A chamber sense may be either an atrial sense or a ventricular sense depending on whether it occurs in the atrial or ventricular sensing channel. Pacing algorithms used in particular pacing modes employ such senses to trigger or inhibit pacing. Both bradycardia and anti-tachycardia pacing modes may be implemented in code executed by the controller.

2. Anti-Tachycardia Pacing

The cardiac rhythm management device of FIG. 1 may be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy attempt to block the reentrant depolarization wavefront causing the tachycardia with depolarizing wavefronts produced by a burst of pacing pulses. (A burst, as the term is used herein, may consist of one or more pacing pulses.) Protocols may vary according to parameters that define the number of pulses delivered and the particular timing employed. For example, the protocol may define a burst of pulses delivered at a specified pacing interval (or with varying pacing intervals) and for a specified time. The protocol may further define the duration and amplitude of the pacing pulses. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy.

The device delivers ATP therapy or a defibrillation shock under programmed control of the microprocessor in response to sensed activity from the sensing channels. A sensing routine analyzes the electrical activity received from the sensing channels in order to detect a tachyarrhythmia, and the tachyarrhythmia is then classified as a tachycardia (i.e., a terminable tachyarrhythmia) or fibrillation based upon rate and/or other criteria. The device detects a ventricular tachyarrhythmia, for example, by counting ventricular senses received via the ventricular sensing channel in order to measure the heart rate and determine whether the rate exceeds a selected threshold value. Once a tachyarrhythmia is detected, the rhythm is classified into either a tachycardia or a fibrillation zone by comparing the heart rate to a fibrillation rate boundary or by other means such as assessing the stability of the rhythm. If the tachyarrhythmia is classified as terminable, a pacing routine executed by the microprocessor delivers ATP pulses in accordance with the parameters of a selected protocol.

As noted above, the object of anti-tachycardia pacing is to create one or more pace-induced wavefronts that propagate into the re-entrant circuit of the tachycardia and extinguish it. In order for a pacing pulse to have any effect, the pulse must capture the ventricle so that a propagating depolarization results. This is complicated by the fact that during a ventricular tachyarrhythmia, the action potential consumes a large portion of the total cycle length, leaving only a small window of time when the ventricle is non-refractory and even less time for an induced depolarization wavefront to propagate into the re-entrant circuit. One adjustable ATP parameter is the coupling interval, which is the time from the last sensed depolarization to the first pacing pulse of a burst, commonly selected to be between 120 and 750 milliseconds. For capture to be achieved by that pacing pulse, the end of the coupling interval must occur when the ventricle is non-refractory. In a so-called scan mode, some devices vary the coupling interval of a series of bursts in a predetermined manner. When the ATP pacing burst consists of a train of pulses, the time between the pulses or cycle length is another parameter that can be adjusted as in a ramp-type burst where the cycle length increases or decreases with each pulse of the train.

3. Monitoring of Entrainment

The efficacy of ATP therapy is dependent upon the extent to which the heart is entrained by the ATP pulses, where entrainment refers to the capturing of the heart by successive pacing pulses. It would be useful for the device to monitor the extent of entrainment during delivery of ATP therapy and then use that information to automatically adjust the manner in which the therapy is delivered. Sensed electrical activity in a heart chamber resulting from a pace, referred to as an evoked response, may be used to verify that capture was achieved by an ATP pulse. The extent of entrainment may then be determined by counting the number of successive pulses which are successful in achieving capture. An evoked response sensing channel, which may be a dedicated channel as shown in FIG. 1 or a sensing channel normally used to sense intrinsic activity, is used to determine whether a pacing pulse has captured the heart chamber by detecting whether or not an evoked response occurs as a result of a pacing pulse. The particular channel used for evoked response detection should be one whose electrode is disposed in a location where an evoked response due to the pacing electrode can be most easily sensed. A ventricular sensing/pacing channel or a dedicated evoked response sensing channel with an electrode disposed in the paced ventricle, for example, could be used to detect evoked responses to ventricular paces.

In order to detect an evoked response, the sense signal generated by the evoked response sensing channel after a pacing pulse is compared with an evoked response detection threshold, which may be the same or different as the intrinsic detection threshold used to detect chamber senses. The evoked response detection threshold may also be adaptively adjusted as described in U.S. Pat. No. 6,192,275 issued to Zhu et al., and assigned to Cardiac Pacemakers, Inc., which is hereby incorporated by reference. The comparison between the sense signal and the evoked response detection threshold takes place within a defined period of time following output of the pacing pulse, referred to herein as a capture detection window. After a pacing pulse is output, an evoked response is either detected or not, signifying the presence or loss of capture, respectively.

Sensing channels are normally rendered refractory (i.e., insensitive) for a specified time period immediately following a pace in order to prevent the pacemaker from mistaking a pacing pulse or afterpotential for an intrinsic beat. To implement this function, the pacemaker controller ignores what would otherwise be detected chamber senses in the channel during the refractory interval. If the same sensing channel is used for both sensing intrinsic activity and evoked responses in a chamber, the capture detection window is then further defined as a period that supercedes the normal refractory period so that the pacemaker is sensitive to an evoked response even if no intrinsic events can be detected. For example, a ventricular sensing/pacing channel may be used to deliver ventricular paces, sense intrinsic ventricular beats, and detect evoked responses. During the capture detection window following a ventricular pace, the controller is prevented from detecting a ventricular sense but can still detect an evoked response if the sense signal exceeds the evoked response detection threshold.

It is also common practice to block the sensing amplifier of a sensing channel from receiving sense signals for a defined period of time that starts with a pacing pulse that is delivered through the same or a different channel, referred to as blanking. This is done in order to prevent saturation of the amplifier by the high voltage signal resulting from a pacing pulse. A separate period of time that overlaps the early part of a refractory interval is therefore defined, called a blanking interval, during which the sense amplifiers are effectively disabled. If a blanking interval is employed in an evoked response sensing channel, the blanking interval is followed by a capture detection window during which an evoked response may be detected by the evoked response sensing channel. In an exemplary embodiment, the blanking period may be approximately 10 ms, and the width of the capture detection window may range from 50 to 350 ms.

4. Adjustment of ATP Therapy in Accordance with Entrainment Monitoring

When the heart is entrained by a sequence of ATP pulses, there is a fixed 1:1 relationship between the pacing pulses of the sequence and subsequently detected evoked responses. By monitoring the extent of entrainment, the device is able to adjust the manner in which the ATP therapy is delivered and increase the probability that it will be successful, thus avoiding the need for shock therapy. In an exemplary embodiment, the device is programmed to deliver a burst of ATP pulses in accordance with a predetermined protocol after detecting a terminable tachyarrhythmia. The burst could be, for example, a fixed programmable number N of pulses (e.g., 8) each separated by a specified pacing interval or a ramp-type burst in which the pacing interval varies during the burst. The burst is delivered after a specified coupling interval following a sense in the heart chamber in which the tachyarrhythmia is occurring. The device is then programmed to count the number of successive pacing pulses during the burst which were successful in achieving capture. If this number is greater than or equal to a specified number M (e.g., 5), referred to as the entrainment threshold number, the device deems the heart to have been entrained during the burst. The device may then be further programmed to adjust the ATP therapy in a manner depending upon whether or not entrainment occurred. In one embodiment, if the device detects entrainment during the ATP burst, the burst is terminated. That is, if M successive pacing pulses have achieved capture before the specified number of pacing pulses in the burst (i.e., N where N>M) has been output, the device ceases pacing. If the tachyarrhythmia persists, the entrainment threshold number M may be increased for the next burst. If no entrainment is detected during the burst and the tachyarrhythmia persists, the device may change the ATP protocol for subsequent bursts by, for example, shortening or lengthening the coupling interval, adjusting the pacing interval or intervals during the burst, changing the number of pulses in the burst, or adjusting the pacing pulse energy.

Figure 2:
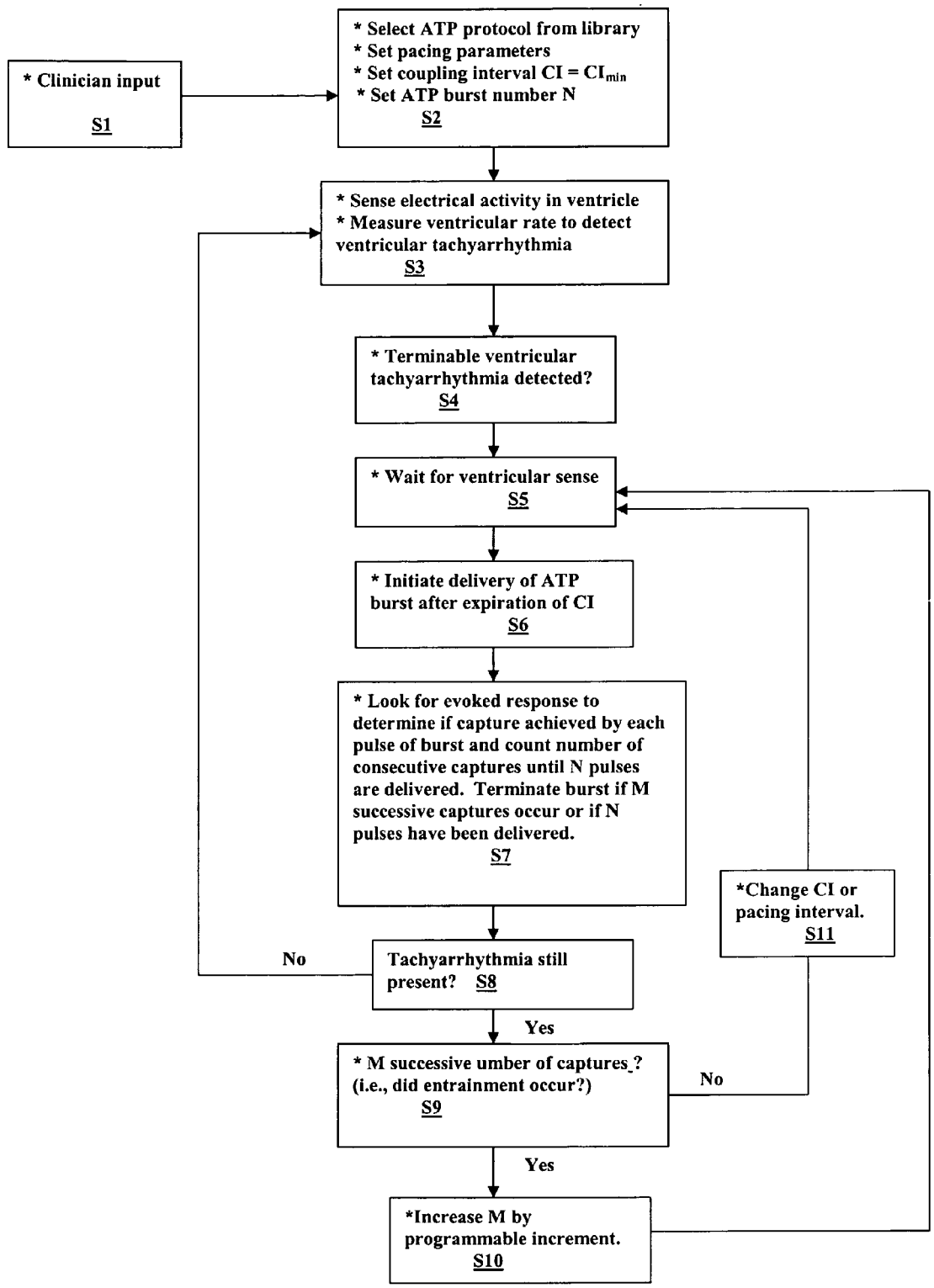
FIG. 2 is a flow diagram showing the steps performed in a particular implementation.

FIG. 2 is a flow diagram showing the steps performed by a cardiac rhythm management device in one particular algorithm for delivering ventricular ATP therapy. (A similar algorithm could be performed to deliver atrial ATP therapy.) The device is set up for delivering anti-tachycardia pacing therapy at step S2 where a particular ATP protocol is selected and various pacing parameter values are set, including the coupling interval CI and the number of pulses in an ATP burst. In this embodiment, the coupling interval is initially set to a specified minimum value $CI_{min}$ and the number of pulses in a burst is set to N. Clinician input for the set up procedure may be received via telemetry is received at step S1. At step S3, the device begins monitoring electrical activity in a ventricle via a sensing channel and counts ventricular senses to determine the ventricular rate. Using a rate-based criterion, the ventricular rate is classified as a terminable tachyarrhythmia when it falls within a specified zone. If a terminable tachyarrhythmia is detected at step S4, the device begins to deliver ATP therapy. The device then waits for the next ventricular sense at step S5 and starts a timer for the coupling interval CI. After expiration of the coupling interval, an ATP burst is delivered at step S6. As the term is used herein, a burst may consist of only one pacing pulse or a series of pacing pulses separated by a time interval referred to as the cycle length. In the latter case, the coupling interval is measured with respect to the initial pulse of the series. At step S7, the device looks for an evoked response after each pulse of the burst through a ventricular evoked response channel in order to determine if the pulse captured the ventricle and counts the number of captures until the maximum number of pulses in the burst N is reached. The ATP burst is terminated before N pulses have been delivered if M number of successive pacing pulses have achieved capture, where M is the programmable entrainment threshold number. At step S8, ventricular activity is monitored to see whether or not the tachyarrhythmia is still present. If not, the device returns to step S3 to continue monitoring. If the tachyarrhythmia has persisted, the device determines whether entrainment occurred during the burst by comparing the number of successive capturing pacing pulses to the entrainment threshold M at step S9. If entrainment occurred, the entrainment threshold number M is increased by a programmable increment (e.g., 1) at step S10, and the device returns to step S5 to deliver another ATP burst. If no entrainment occurred, the coupling interval and/or the pacing interval are adjusted at step S11 before returning to step S5.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for delivery of anti-tachycardia pacing (ATP) therapy by a cardiac rhythm management device, comprising:
   generating sense signals representing electrical activity in a heart chamber and detecting a chamber sense when a sense signal exceeds a specified intrinsic detection threshold;
   detecting a tachycardia in the heart chamber when a rate at which chamber senses are detected exceeds a specified tachycardia threshold value;
   upon detection of a tachycardia, delivering a burst of pacing pulses in accordance with an anti-tachycardia pacing protocol, where the burst is output after a specified coupling interval with respect to a chamber sense;
   determining if a pacing pulse has captured the heart chamber by detecting whether an evoked response occurs during a capture detection window following the output of a pacing pulse; and,
   determining the extent to which the heart chamber has been entrained by counting the number of consecutive pacing pulses during the burst that achieve capture without an intervening loss of capture to thereby determine the number of successive pacing pulses achieving capture during the burst.

2. The method of claim 1 further comprising comparing the number of successive pacing pulses which achieve capture during the burst to an entrainment threshold number M.

3. The method of claim 2 further comprising terminating the burst when M successive pacing pulses have achieved capture.

4. The method of claim 3 further comprising increasing the entrainment threshold number M for a subsequent burst if the tachyarrhythmia persists.

5. The method of claim 2 further comprising increasing the coupling interval for a subsequent burst if the tachyarrhythmia persists and the number of successive pacing pulses achieving capture in a previous burst was less than M.

6. The method of claim 2 further comprising decreasing the coupling interval for a subsequent burst if the tachyarrhythmia persists and the number of successive pacing pulses achieving capture in a previous burst was less than M.

7. The method of claim 1 wherein the delivered burst is a train of pacing pulses separated by a specified cycle length.

8. The method of claim 7 wherein the burst is a ramp-type burst such that the cycle length between pacing pulses is progressively shortened with each pulse in the burst.

9. The method of claim 2 wherein the delivered burst is a train of pacing pulses separated by a specified cycle length and further comprising adjusting the cycle length for a subsequent burst if the tachyarrhythmia persists and the number of successive pacing pulses achieving capture in a previous burst was less than M.

10. The method of claim 2 wherein the delivered burst is a train of pacing pulses separated by a specified cycle length and further comprising adjusting the pacing pulse energy for a subsequent burst if the tachyarrhythmia persists and the number of successive pacing pulses achieving capture in a previous burst was less than M.

11. A cardiac rhythm management device, comprising:
   a sensing channel for generating sense signals representing electrical activity in a heart chamber and detecting a chamber sense when a sense signal exceeds a specified intrinsic detection threshold;
   a pacing channel for delivering anti-tachycardia pacing therapy;
   a controller interfaced to the sensing and pacing channel, wherein the controller is programmed to:
   detect a tachycardia in the heart chamber when a rate at which chamber senses are detected exceeds a specified tachycardia threshold value;
   upon detection of a tachycardia, deliver a burst of pacing pulses in accordance with an anti-tachycardia pacing protocol, where the burst is output after a specified coupling interval with respect to a chamber sense;
   determine if a pacing pulse has captured the heart chamber by detecting whether an evoked response occurs during a capture detection window following the output of a pacing pulse; and,
   determine the extent to which the heart chamber has been entrained by counting the number of consecutive pacing pulses during the burst that achieve capture without an intervening loss of capture to thereby determine the number of successive pacing pulses achieving capture during the burst.

12. The device of claim 11 wherein the controller is further programmed to compare the number of successive pacing pulses which achieve capture during the burst to an entrainment threshold number M.

13. The device of claim 12 wherein the controller is further programmed to terminate the burst when M successive pacing pulses have achieved capture.

14. The device of claim 13 wherein the controller is further programmed to increase the entrainment threshold number M for a subsequent burst if the tachyarrhythmia persists.

15. The device of claim 12 wherein the controller is further programmed to increase the coupling interval for a subsequent burst if the tachyarrhythmia persists and the number of successive pacing pulses achieving capture in a previous burst was less than M.

16. The device of claim 12 wherein the controller is further programmed to decrease the coupling interval for a subsequent burst if the tachyarrhythmia persists and the number of successive pacing pulses achieving capture in a previous burst was less than M.

17. The device of claim 11 wherein the delivered burst is a train of pacing pulses separated by a specified cycle length.

18. The device of claim 17 wherein the burst is a ramp-type burst such that the cycle length between pacing pulses is progressively shortened with each pulse in the burst.

19. The device of claim 12 wherein the delivered burst is a train of pacing pulses separated by a specified cycle length and wherein the controller is further programmed to adjust the cycle length for a subsequent burst if the tachyarrhythmia persists and the number of successive pacing pulses achieving capture in a previous burst was less than M.

20. The device of claim 12 wherein the delivered burst is a train of pacing pulses separated by a specified cycle length and wherein the controller is further programmed to adjust the pacing pulse energy for a subsequent burst if the tachyarrhythmia persists and the number of successive pacing pulses achieving capture in a previous burst was less than M.

* * * * *